United States Patent [19]

Bertolini et al.

[11] Patent Number: 5,426,179
[45] Date of Patent: Jun. 20, 1995

[54] STEROID COMPOUNDS ACTIVE ON THE CARDIOVASCULAR SYSTEM

[75] Inventors: Giorgio Bertolini, Sesto san Giovanni; Cesare Casagrande, Arese; Stefania Montanari, Milan; Gabriele Norcini, Maddalena Somma Lombardo; Francesco Santangelo, Milan, all of Italy

[73] Assignee: Zambon Group S.p.A., Vicenza, Italy

[21] Appl. No.: 834,769

[22] Filed: Feb. 12, 1992

[30] Foreign Application Priority Data

Feb. 14, 1991 [IT] Italy .................. MI91A0380

[51] Int. Cl.[6] .................. C07J 19/00; C07J 53/00; A61K 31/705
[52] U.S. Cl. .................. 536/5; 536/6.1; 540/15; 540/17; 540/23; 540/41; 552/508
[58] Field of Search .................. 536/5, 6.1; 514/169, 514/175, 178, 179, 26; 540/23, 41, 15, 17; 552/508

[56] References Cited

U.S. PATENT DOCUMENTS 3,968,132 7/1976 Green et al. .................. 540/41

FOREIGN PATENT DOCUMENTS 0018245 10/1980 European Pat. Off. .
2546779 4/1977 Germany .

OTHER PUBLICATIONS

Chemical Abstracts, vol. 100, No. 15, 9 Apr. 1984, US, Abstract No. 121435, C. Lindig, "Partial Synthesis of . . . ".
Brown et al.; Arzneim.-Forsch./Drug Res. 31 (II) No. 7:1059–1064 (1981).
The Merck Index 10th ed (1983) p. 459.
Beloeil et al.; Tetrahedron 39(23):3937–3941 (1983).
Templeton et al.; Can. J. Physiol. Pharmacol. 66:1420–24 (1988).
Noel et al.; Biochem. Pharmacol. 40(12):2611–2616 (1990).

*Primary Examiner*—Douglas W. Robinson
*Assistant Examiner*—Howard C. Lee
*Attorney, Agent, or Firm*—Stevens, Davis, Miller & Mosher

[57] ABSTRACT

Steroid compounds active on the cardiovascular system of formula

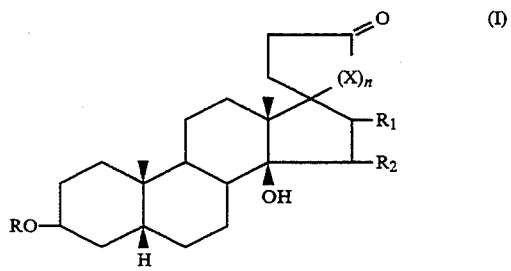

wherein X, n, R, $R_1$ and $R_2$ have the meanings mentioned in the description are described.

6 Claims, No Drawings

STEROID COMPOUNDS ACTIVE ON THE CARDIOVASCULAR SYSTEM

DESCRIPTION

This invention relates to steroid compounds active on the cardiovascular system and, more specifically, to cardioactive derivatives of 14beta-hydroxy-5beta androstane of formula

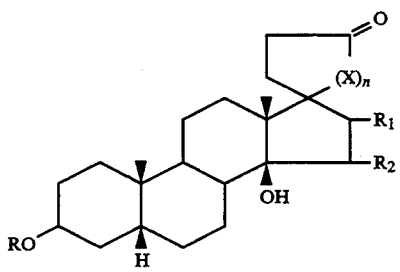

wherein
n is 0 or 1;
R is hydrogen or a glycosyl residue;
$R_1$ and $R_2$ are hydrogen or together they form a covalent bond; and
substituents in position 5, 10, 13 and 14 have beta configuration.

The compounds of this invention are useful in the treatment of pathologies of the cardiovascular system and, in particular, heart failure and hypertension.

Typical examples of glycosyl residues are: monosaccharides such as D-glucose, D-lyxose, D-xylose, 2-deoxy-D-glucose, D-allomethylose, D-thevetose, L-thevetose, L-talomethylose, D-gulomethylose, D-glucomethylose, L-rhamnose, L-acofriose, D-fucose, L-fucose, D-digitalose, L-acovenose, D-digitoxose, D-cymarose, D-boivinose, D-sarmentose, L-oleandrose, D-oleandrose, D-diginose or di- and trisaccharides consisting respectively of two or three monosaccharides among those cited.

Examples of compounds of formula I are

I-A

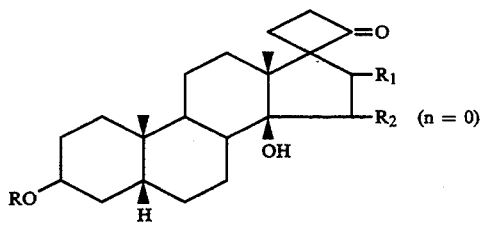

and

I-B

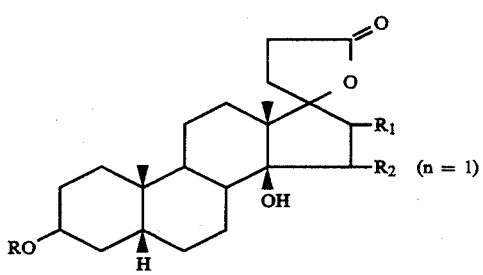

in which R, $R_1$ and $R_2$ have the above mentioned meanings.

The process for the preparation of the compounds of formula I is shown in the following diagram 1.

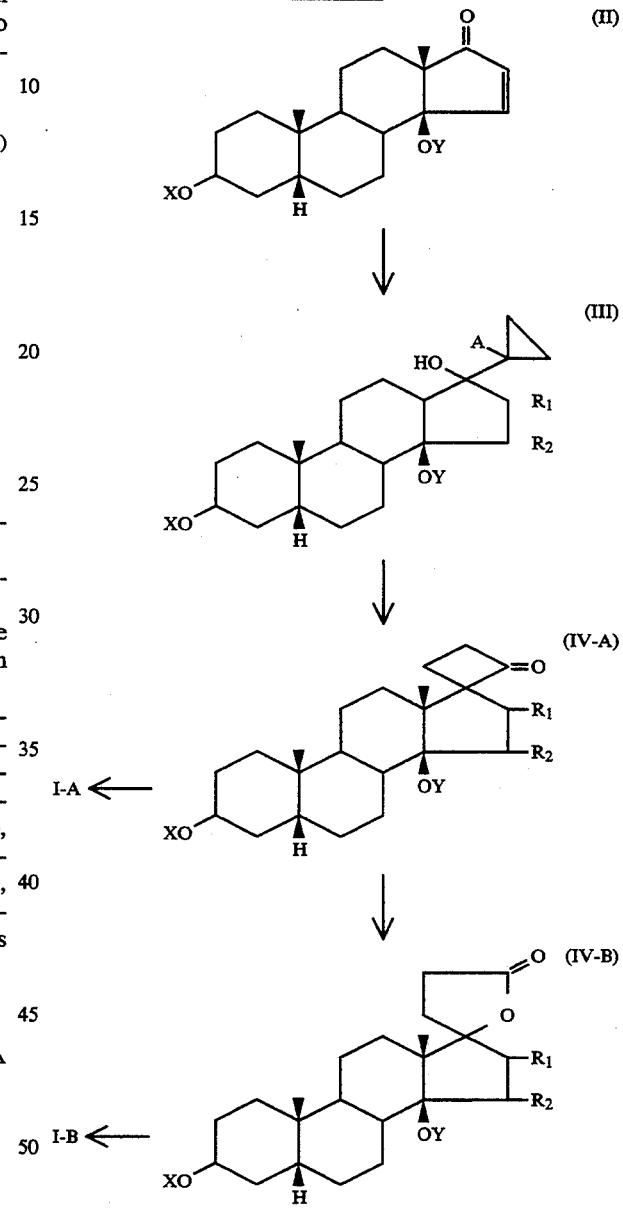

in which
$R_1$ and $R_2$ have the above mentioned meanings;
X has the same meaning as R or is a protective group;
Y is hydrogen or a protective group;
A is a phenylthio or an ethoxy group.

Ketoderivatives of formula II are known compounds or are easily prepared according to known methods such as the one described by Beloeil et al., Tetrahedron 39 (23), (3937–41, (1983) or from digitoxigenin.

Preferably, there are used compounds of formula II in which X and Y are protective groups such as, for instance, benzyl, acetyl, trimethylsilyl and ethoxymethoxy groups.

Starting compounds of formula II are made to react with the anion of a suitable cyclopropyl derivative which is usually prepared "in situ" by treatment of a compound of formula

  (V)

wherein X is hydrogen or halogen and A has the above mentioned meanings; with an alkyl lithium compound, such as n-butyl lithium and t-butyl lithium, in a suitable organic solvent.

Unsaturated compounds of formula III (in which $R_1$ and $R_2$ form a covalent bond) are thus formed which can be directly reduced to yield the corresponding saturated compounds (III, $R_1=R_2=H$).

The reduction is accomplished with hydrogen in the presence of catalysts such as palladium, platinum, rhodium, and iridium.

The person skilled in the art will appreciate that the reduction of the double bond can be accomplished, as an alternative, even in the subsequent steps of the process, that is on the intermediates of formula IV or the final products of formula I.

The intermediates of formula III transpose to the corresponding spirocyclobutanones of formula IV-A by treatment with acids such as p-toluenesulfonic acid, in tetrachloride, silica gel, tetrafluoroboric acid, camphorsulfonic acid, possibly after conversion of the hydroxy group in position 17 into the corresponding phosphite or phosphate.

The compounds of formula I-A are obtained according to conventional techniques from the spirocyclobutanones IV-A, wherein Y is different from hydrogen.

For example, compounds IV-A in which X and Y are protective groups become unprotected by hydrogenation or hydrolysis.

Hence it becomes clear that, depending on the preselected conditions of the reaction, the becoming unprotected can be suitably accomplished even at the level of the intermediates preceding the synthesis.

The compounds of formula I-A in which R is hydrogen are obtained by becoming unprotected. From these (I-A, R=H), the coresponding compounds I-A in which R is a glycosyl residue are prepared according to conventional glycosylation reactions.

Among the glycosylation methods known in literature, we shall cite as an example: Schmidt, Angew, Chem. Int. Ed. Engl. 25 (1986), 212; Paulsen, Angew, Chem. Int. Ed. Engl. 21 (1982), 155; Weisner et al., Helv. Chim. Acta 68 (1985), 300.

The compounds of formula IV-A are useful intermediates for prepararing the spirolactones of formula IV-B.

The transformation of compounds IV-A to the corresponding compounds IV-B can be accomplished by means of the Bayer-Villiger oxidation with peracids or hydrogen peroxide.

Similarly to what has been reported for compounds IV-A, compounds IV-B yield spirolactones I-A by deprotection and subsequent glycosylation.

Alternatively, the compounds of formula I-B in which $R_1$ and $R_2$ are hydrogen are prepared according to the process shown in the following diagram 2.

Diagram 2

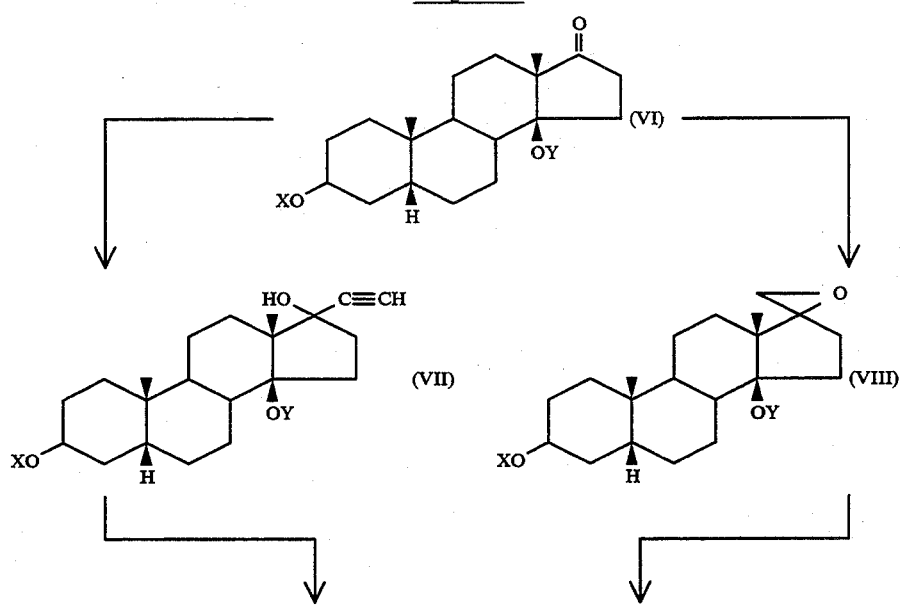

Diagram 2
-continued

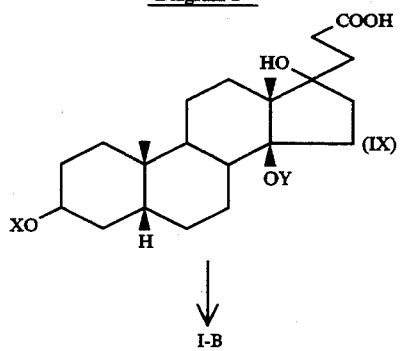

wherein X and Y have the above mentioned meanings.

The ketoderivatives of formula VI are known or easily prepared with conventional methods [Sondheimer et al., J. Am. Chem., Soc., 91 (5), 1228–30, (1969)].

By reaction with lithium acetylide or lithium trimethyl silyl acetylide, the intermediate VI yields compound VII which, by carboxylation and subsequent reduction, allows the formation of the gamma-hydroxyacid of formula IX.

The lactone formation reaction, followed by subsequent unprotection and glycosylation according to what has already been reported, to yield the spirolactones I-B is accomplished by the treatment of compounds IX with weak acids or under dehydrating conditions such as for instance in the presence of molecular sieves, in organic solvents.

Alternatively, the intermediates IX can be prepared through the formation of the epoxy compound of formula VIII. This is prepared from the keto derivative VI, by for instance, a reaction with dimethyl sulfonyl methyl in tetrahydrofuran.

The epoxy VIII is then made to react with lithium acetonitrile thus yielding a gamma-hydroxynitrile which is then hydrolyzed in a basic medium to the corresponding acid IX.

Compounds of formula I possess positive contractile inotropic activity, vasodilating activity, and also produce renal effects by increasing perfusion, diuresis and the excretion of sodium.

It is known that cardiac glycosides such as ouabain exert their activity through inhibition of the (Na+/K+)-ATPase enzyme (Goodman and Gilman's, "The Pharmacological Basis of Therapeutics", eighth edition, pages 814–839).

Inhibition of this enzyme causes an increase in the intracellular Na+ thus inducing an increase in the Ca++ concentration through Na+/Ca++ exchange.

This phenomenon is therefore responsible for the contraction of the cell.

Many (Na+/K+)-ATPase isoenzymes are also known (Noel F. et al., Biochemical Pharmacology, 40, No. 12, 2611–2616, 1990).

With respect to ouabain, the compounds of this invention proved to have the same affinity or more for alpha-1 isoenzyme of the kidney of the rat while having less affinity for alpha-3 isoenzyme of the brain of the rat.

This selective affinity is useful in the cardiovascular pathologies such as hypertension and heart or kidney insufficiency.

The compounds of this invention are therefore useful in the therapy of pathologies of the cardiovascular system and, in particular, the treatment of heart failure and hypertension.

For practical application in therapy, the compounds of formula I are formulated in pharmaceutical forms suitable for oral and parenteral administration.

The therapeutic doses are generally in amounts of from 1 and 100 mg/day.

Therefore, a further object of this invention is to provide pharmaceutical compositions containing a therapeutically effective amount of a compound of formula I together with a pharmaceutical carrier.

The compositions of this invention are prepared according to conventional techniques.

The following examples are intended to further illustrate this invention without limiting it in any way.

EXAMPLE 1

Preparation of digitoxigenin-3,14-di-(ethoxymethyl)-ether

At a temperature of about 0° C., ethoxy methyl chloride (12.4 ml; 133.7 mmoles) was added dropwise to a solution of digitoxigenin (5 g; 13.37 mmoles) and diisopropyl ethylamine (51.7 ml; 401.1 mmoles) in methylene chloride (150 ml).

When the addition was over, the solution was refluxed for 8 hours.

After cooling to room temperature, methylene chloride (50 ml) was added and three washings have been carried out with a solution of dilute citric acid followed by one washing with water.

The organic phase was dried over sodium sulfate and the solvent was evaporated under reduced pressure.

The crude oily residue was purified by chromatography on silica gel (eluent, hexane:ethyl acetate=1:1).

The pure product was obtained as an oil which tends to solidify (5.96 g).

$^1$H-NMR (400 MHz, CDCl$_3$): delta (ppm): 0.90 (s, 3H); 0.95 (s, 3H); 1.21 (bt, 6H); 2.70 (bt, 1H); 3.50–3.68 (2m, 2H); 3.62 (q, 2H); 3.92 (bs, 1H); 4.70 (d, 1H); 4.71 (s, 2H); 4.82 (d, 1H); 4.84 (q, 2H); 5.89 (s, 1H).

By working in a similar way but using neriifolin, (3beta,5beta)-3-[[6-deoxy-2,4-di-(ethoxymethyl)-3-O-methyl-alpha-L-glucopyranosyl]oxy]-14-ethoxymethoxy-card-20(22)-enolide was prepared.

m.p. 55°–57° C. $^1$H-NMR (300 MHz, CDCl$_3$): delta (ppm): 0.90 (s, 3H); 0.97 (s, 3H); 1.21 (3t+1d, 12H); 1.10–2.20 (m, 22H); 2.69 (m, 1H); 3.13 (m, 1H); 3.40–3.80 (m, 8H); 3.70 (s, 3H); 3.88 (bs, 1H); 4.73 (dd, 2H); 4.75 (s, 2H); 4.81 (m, 2H); 4.85 (dd, 2H); 4.86 (m, 1H); 5.89 (bs, 1H).

EXAMPLE 2

Preparation of 1-hydroxy-digitoxigenin-3,14-di-(ethoxymethyl)-ether

A solution of digitoxigenin-3,14-(ethoxymethyl)-ether (5 g; 10.2 mmoles), prepared as described in Example 1, and selenium dioxide (4.25 g; 38.2 mmoles) in dioxane (1 l) was refluxed by 6 hours with stirring.

The mixture was cooled to room temperature, filtered, concentration under reduced pressure up to about ⅓ of the initial volume, poured into water and extracted with methylene chloride. The organic phase was separated with water and dried over sodium sulfate.

After evaporation of the solvent under reduced pressure, the crude residue was purified by chromatography on silica gel (eluent, hexane:ethyl acetate=8:2) thus obtaining the pure product (4.76 g).

$^1$H-NMR (400 MHz, CDCl$_3$): delta (ppm): 0.92 (s, 3H); 0.98 (s, 3H); 1.18 (t, 3H); 1.21 (t, 3H); 2.25 (m, 1H); 2.46 (m, 1H); 3.45 (m, 1H); 3.62 (q, 2H); 3.64 (m, 1H); 3.93 (bs, 1H); 4.50 (d, 1H); 4.71 (s, 2H); 4.81 (d, 1H); 4.84 (d, 1H); 5.12 (d, 1H); 6.13 (s, 1H).

By working in a similar way (3beta,5beta)-3-[[6-deoxy-2,4-di(ethoxymethyl)-3-O-methyl-alpha-L-glucopyranosyl]oxy]-14-ethoxymethoxy-17-hydroxy-card-20(22)-enolide was prepared.

m.p. 160°–165° C. $^1$H-NMR (300 MHz, CDCl$_3$): delta (ppm: 0.91 (s, 3H); 0.97 (s, 3H); 1.21 (m, 12H); 1.10–2.05 (m, 20H); 2.24 (m, 1H); 2.43 (m, 1H); 3.12 (m, 1H ); 3.30–3.81 (m, 8H); 3.56 (s, 3H); 3.88 (bs, 1H); 4.63 (dd, 2H); 4.75 (s, 2H); 4.84 (dd, 2H); 4.85 (bs, 1H); 4.96 (ddd, 2H); 6.11 (m, 1H).

EXAMPLE 3

Preparation of 3beta,14-di-(ethoxymethoxy)-5beta,14beta-androstan-17-one

Aliquots of powdered potassium permanganate (1.20 g) were added to a solution of 17-hydroxy-digitoxigenin-3,14-(ethoxymethyl)-ether (0.5 g; 0.99 mmoles), prepared as described in Example 2, in acetone (50 ml), kept under vigorous stirring and at a temperature of about 25° C.

After about 1 hour, the mixture was filtered over celite and the solvent was evaporated under reduced pressure.

Methylene chloride (50 ml) was added to the residue and the insoluble portion was eliminated by filtration.

After evaporation of the solvent, the crude residue was purified by chromatography on silica gel (eluent, hexane:ethyl acetate=6:4)thus obtaining a pure product (0.27 g).

$^1$H-NMR (400 MHz, CDCl$_3$): delta (ppm): 0.96 (s, 3H); 1.08 (s, 3H); 1.16 (t, 3H); 1.21 (t, 3H); 2.19 (m, 1H); 2.24 (m, 1H); 2.50 (m, 2H); 3.52 (m, 2H); 3.61 (q, 2H); 3.93 (bs, 1H); 4.56 (d, 1H); 4.70 (s, 2H); 4.85 (d, 1H).

By working in a similar way 3beta-[[6-deoxy-2,4-di(ethoxymethyl)-3-O-methyl-alpha-L-glucopyranosyl]oxy]-14-ethoxymethoxy-5beta,14beta-androstan-17-one was prepared.

$^1$H-NMR (300 MHz, CDCl$_3$): delta (ppm): 0.96 (s, 3H); 1.07 (s, 3H); 1.24 (m, 12H); 1.10–2.00 (m, 20H); 2.20 (m, 1H); 2.48 (m, 1H); 3.13 (m, 3.45–3.90 (m, 8H); 3.57 (s, 3H); 4.89 (bs, 1H); 4.68 (dd, 2H); 4.75 (s, 2H); 4.85 (dd, 2H); 4.86 (m, 1H).

EXAMPLE 4

Preparation of 3-beta-ethoxymethoxy-14-hydroxy-5beta,14beta-androstan-17-one A solution of 3beta,14-di-(ethoxymethoxy)-5beta,14beta-androstan-17-one (50 mg; 0.118 mmoles), prepared as described in Example 3, in methanol (3 ml) and hydrochloride acid 1N (1 ml) was left at 25° C. for 45 minutes.

After the addition of water (5 ml) and extraction with ethyl acetate, the organic phase was dried over sodium sulfate.

By evaporation of the solvent under reduced pressure the pure product was obtained (36 mg) as a colorless oil.

$^1$H-NMR (300 MHz, CDCl$_3$): delta (ppm): 0.96 (s, 3H); 1.06 (s, 3H); 1.22 (t, 3H); 1.20–2.30 (m); 2.43 (m, 2H); 3.62 (q, 2H); 3.94 (bs, 1H); 4.72 (s, 2H).

By working in a similar way 3beta-[[6-deoxy-2,4-di-(ethoxymethyl)-3-O-methyl-alpha-L-glucopyranosyl]oxy]-14-hydroxy-5beta,14beta-androstan-17-one was prepared.

$^1$H-NMR (300 MHz, CDCl$_3$); delta (ppm): 0.97 (s, 3H); 1.05 (s, 3H); 1.11 (t, 3H); 1.14 (t, 3H); 1.15 (d, 3H); 1.10–1.90 (m, 19H); 2.20 (m, 1H); 2.41 (m, 2H); 3.13 (m, 1H); 3.50–3.84 (m, 6H); 3.58 (s, 3H); 3.90 (bs, 1H); 4.75 (s, 2H); 4.86 (dd, 2H); 4.87 (d, 1H).

EXAMPLE 5

Preparation of 17-spiro-oxirane-3beta-ethoxymethoxy-14-hydroxy-5beta,14beta-androstane A solution of trimethylsolfonium iodide (255 mg; 1.1 mmoles) in anhydrous dimethylsulfoxide (0.96 ml) was added to a solution of dimsylosodium 2M in dimethylsulfoxide (0.55 ml; 1.1 mmoles) and anhydrous tetrahydrofuran (2.5 ml) at 0° C. under nitrogen atmosphere.

After 5 minutes under stirring, a solution of 3beta-ethoxymethoxy-14-5beta-androstan-17-one (100 mg; 0.276 mmoles), prepared as described in Example 4, in anhydrous tetrahydrofuran (1 ml) was added and the mixture was stirred for 2 hours at 25° C.

The reaction mixture was poured in water (5 ml) and extracted with ethyl acetate.

The separated organic phase was dried over sodium sulfate.

The crude residue obtained after evaporation of the solvent under reduced pressure was chromatographed on silica gel (eluent, hexane:ethyl acetate=7:3) thus yielding the pure product (53 mg).

$^1$H-NMR (300 MHz, CDCl$_3$): delta (ppm): 0.75 (s, 3H); 0.98 (s, 3H); 1.22 (t, 3H); 1.20–2.00 (m); 2.08 (m, 1H); 2.28 (m, 1H); 2.60 (d, 1H); 2.71 (d, 1H); 3.63 (q, 2H); 3.93 (bs, 1H); 4.72 (s, 2H).

By working in a similar way 3beta-[[6-deoxy-2,4-di-(ethoxymethyl)-3-O-methyl-alpha-L-glucopyranosyl]oxy]-14-hydroxy-17(R)-spiro-oxirane-5beta,14beta-androstane was prepared.

$^1$H-NMR (300 MHz, CDCl$_3$): delta (ppm): 0.73 (s, 3H); 0.97 (s, 3H); 1.19 (t, 3H); 1.22 (t, 3H); 1.24 (d, 3H); 1.10–2.35 (m, 21H); 2.58 (d, 1H) 2.70 (d, 1H); 3.13 (m, 1H); 3.57 (s, 3H); 3.50–3.80 (m, 7H); 3.89 (bs, 1H); 4.75 (s, 2H); 4.79 (d, 1H); 4.87 (d, 1H); 4.93 (d, 1H).

EXAMPLE 6

Preparation of 17-spiro-oxirane-3beta,14-di(ethoxymethoxy)-5beta,14beta-androstane Diisopropyl ethlamine (26.4 ml; 151 mmoles) and chloromethyl-diethylether (4.64 ml; 50 mmoles) were added to a solution of 17-spiro-oxirane-3beta-ethoxymethoxy-14-hydroxy-5beta,14beta-androstane (1.6 g; 4.23 mmoles), prepared as described in Example 5, in methylene chloride (80 ml).

After 16 hours at room temperature, the solution was poured in water (100 ml) and the organic phase was separated, washed in water and dried over sodium sulfate.

After evaporation of the solvent under reduced pressure, the oily crude residue was chromatographed on silica gel (eluent, hexane:ethyl acetate=8:2) thus obtaining the pure product (1.53 g); a yellow oil.

$^1$H-NMR (300 MHz, CDCl$_3$): delta (ppm): 0.72 (s, 3H); 0.96 (s, 3H); 1.20 (2t, 6H); 1.00–2.10 (m); 2.28 (m, 2H); 2.60 (d, 1H); 2.70 (d, 1H); 3.55–3.72 (2q, 4H); 3.93 (bs, 1HH); 4.72 (s, 2H); 4.86 (d, 1H); 4.93 d, 1H).

By working in a similar way 3beta-[[6-deoxy-2,4-di-(ethoxymethyl)-3-O-methyl-alpha-L-glucopyranosyl]oxy]-14-ethoxymethoxy-17(R)-spiro-oxirane-5beta,14beta-androstane was prepared.

$^1$H-NMR (300 MHz, CDCl$_3$): delta (ppm): 0.12 (s, 3H); 0.96 (s, 3H); 0.70–2.40 (m, 33H); 2.60 (d, 1H); 2.70 (d, 1H); 3.14 (bt, 1H); 3.57 (s, 3H); 3.45–3.80 (m, 9H); 3.88 (bs, 1H); 4.75 (s, 2H); 4.79 (d, 1H); 4.83 (d, 1H); 4.87 (d, 1H); 4.91 9d, 1H); 4.93 (d, 1H).

EXAMPLE 7

Preparation of 17-hydroxy-17-(2-cyanoethyl)-3beta,14-di-(ethoxymethoxy)-5beta,14beta-androstane A solution of n-butyl lithium 1.6M in hexane (0.472 ml; 0.756 mmoles) was added to a solution of diisopropylamine (0.106 ml; 0.756 mmoles) in anhydrous tetrahydrofuran (5 ml), kept at 0° C. under a nitrogen atmosphere.

After 10 minutes the solution was cooled at −60° C. and anhydrous acetonitrile (0.04 ml; 0.756 mmoles) was added.

After half an hour with stirring, a solution of 17-spirooxirane-3beta,14-di-(ethoxymethoxy)-5beta,14beta-androstane (100 mg; 0.229 mmoles), prepared as described in Example 6, in anhydrous tetrahydrofuran (2 ml), was added dropwise.

The temperature was left to rise spontaneously and then the reaction mixture was maintained under stirring for 16 hours at room temperature.

After the addition of water (20 ml) and extraction with ethyl acetate, the separated organic phase was dried over sodium sulfate.

After evaporation of the solvent under reduced pressure, the oily residue was chromatographed on silica gel (eluent, hexane:ethyl acetate=8:2) thus obtaining the pure product (83 mg), as colourless oil.

$^1$H-NMR (300 MHz, CDCl$_3$): delta (ppm): 0.95 (s, 3H); 1.05 (s, 3H); 1.20 (2t, 6H); 1.00–2.10 (m); 2.41 (m, 1H); 2.62 (m, 1H); 3.58 (m, 4H); 3.93 (bs, 1H); 4.39 (d, 1H); 4.72 (s, 2H); 4.77 (d, 1H); 4.94 (d, 1H). I.R. (film): 3500, 2240 cm$^{-1}$.

By working in a similar way 17(S)-3beta-[[6-deoxy-2,4-di-(ethoxymethyl)-3-O-methyl-alpha-L-glucopyranosyl]oxy]-14-ethoxymethoxy-17-hydroxy-17-(cyanoethyl)-5beta,14beta-androstane was prepared.

$^1$H-NMR (300 MHz, CDCl$_3$): delta (ppm): 0.95 (s, 3H); 1.04 (s, 3H); 1.10–2.10 (m, 35H); 2.40 (m, 1H); 2.61 (m, 1H): 3.12 (m, 1H); 3.57 (s, 3H); 3.45–3.82 (m, 9H); 3.88 (bs, 1H); 4.37 (d, 1H, 0H); 4.75 (s, 1H); 4.76 (d, 1H); 4.78 (d, 1H); 4.86 (d, 1H); 4.92 (d, 1H); 4.93 (d, 1H).

EXAMPLE 8

Preparation of 17-hydroxy-17-(2-carboxyethyl)-3beta,14-di-(ethoxymetoxy)-5beta,14beta-androstane A solution of 17-hydroxy-17-(2-cyanoethyl)-3-beta,14-di-ethoxymethoxy)-5beta,14beta-androstane (37 mg; 0.077 mmoles), prepared as described in Example 7, and potassium hydroxide (112 mg, 2 mmoles) in water (1 ml) and methanol (1 ml) was kept under stirring at room temperature for one night and then refluxed for half an hour.

After cooling to room temperature, water (5 ml), ethyl acetate (5 ml), and hydrochloric acid 1N were added with stirring up to pH 1.

The separated organic phase was washed with water and dried over sodium sulfate.

By evaporation of the solvent under reduced pressure the product was obtained as a colourless oil (36 mg).

$^1$H-NMR (300 MHz, CDCl$_3$): delta (ppm): 0.96 (s, 3H); 1.08 (s, 3H); 1.21 (2t, 6H); 1.00–2.10 (m); 2.55 (m, 1H); 2.66 (m, 1H); 3.60 (m, 4H); 4.93 (bs, 1H); 4.72 (s, 2H); 4.79 (d, 1H); 4.96 (d, 1H); 5.26 (bs, 1H). I.R. (film): 3500, 3500–2500, 1770, 1730 cm$^{-1}$.

By working in a similar way 17(S)-3beta-[[6-deoxy-2,4di-(ethoxymethyl)-3-O-methyl-alpha-L-glucopyranosyl]oxy]-14-ethoxymethoxy-17-hydroxy-17-(2-carboxyethyl)-5beta,14beta-androstane was prepared.

$^1$H-NMR (300 MHz, CDCl$_3$): delta (ppm): 0.95 (s, 3H); 1.07 (s, 3H); 1.00–2.20 (m, 35H); 2.50 (m, 1H); 2.65 (m, 3.13 (m, 1H); 3.56 (s, 3H); 3.45–3.80 (m, 9H); 3.70 (bs, 1H); 4.75 (s, 2H); 4.76 (d, 1H); 4.77 (d, 1H); 4.85 (d, 1H); 4.93 (d, 1H); 4.94 (d, 1H).

EXAMPLE 9

Preparation of 17-spiro-(5'-tetrahydrofuran-2'-one)-3-beta,14-di-(ethoxymethoxy)-5beta,14beta-androstane A solution of 17-hydroxy-17-(2-carboxyethyl)-3beta,14-di-(ethoxymethoxy)-5beta,14beta-androstane (20 mg; 0.04 mmoles), prepared as described in Example 8, in anhydrous benzene (3 ml), and kept in contact with molecular sieves (4 A), was refluxed for 6 hours.

After cooling the solution was filtered and the solvent was evaporated under reduced pressure.

The resulting oil was chromatographed on silica gel (eluent, methylene chloride:methanol=9:1) thus obtaining the pure product (11.5 mg).

$^1$H-NMR (300 MHz, CDCl$_3$): delta (ppm): 0.96 (s, 3H); 0.97 9s, 3H); 1.20 (t, 3H); 1.24 (t, 3H); 1.00–2.30 (m); 2.50 (m, 3H); 3.62 (2q, 3H); 3.75 (dd, 1H); 3.93 (bs, 1H); 4.72 (s, 2H); 4.79 (s, 2H). I.R. film: 1760 cm$^{-1}$.

By working in a similar way 3beta-[[6-deoxy-2,4-di-(ethoxymethyl)-3-O-methyl-alpha-L-glucopyranosyl]oxy]-14-ethoxymethoxy-17(S)-spiro-(5'-tetrahydrofuran-2'-one)-5beta,14beta-androstane was prepared.

$^1$H-NMR (300 MHz, CDCl$_3$); delta (ppm): 0.96 (s, 3H); 0.97 (s, 3H); 1.20 (m, 12H); 1.00–2.24 (m, 23H); 2.47 (m, 2H); 3.12 (m, 1H); 3.57 (s, 3H); 3.45–3.82 (m, 9H);

3.87 (bs, 1H); 4.75 (s, 2H); 4.77 (s, 2H); 4.79 (d, 1H); 4.86 (d, 1H); 4.93 (d, 1H).

EXAMPLE 10

Preparation of 17-spiro-(5'-tetrahydrofuran-2'-one)-3beta14-dihydroxy-5beta,14-beta-androstane A solution of 17-spiro-(5'-tetrahydrofuran-2'-one)-3beta,14-di(ethoxymethoxy)-5beta,14beta-androstane (170 mg; 0.193 mmoles), prepared as described in Example 9, in acetone (4 ml) and hydrochloric acid 1N (3 ml) was left at room temperature for 16 hours.

The solution was then poured into water (5 ml) and extracted with ethyl acetate.

The separated organic phase was dried over sodium sulfate and the solvent was evaporated under reduced pressure.

The crude residue was crystallized from a mixture of hexane:ethyl acetate=1:1 thus obtaining the pure product (54 mg).

m.p. 200°-204° C. $^1$H-NMR (300 MHz, CDCl$_3$): delta (ppm): 0.96 (s, 6H); 0.80–2.30 (m); 2.56 (m, 2H); 4.12 (bs, 1H ). I.R. (CHCl$_3$): 3500, 1770 cm$^{-1}$.

By working in a similar way 3beta-[[6-deoxy-3-O-methyl-alpha-L-glucopyranosyl]oxy]-14-hydroxy-17(S)-spiro-(5'-tetrahydrofuran-2'-one)-5beta,14beta-androstane was prepared.

m.p. 218°-220° C. $^1$H-NMR (300 MHz, CDCl$_3$): delta (ppm): 0.97 (s, 3H); 0.98 (s, 3H); 1.25 (d, 3H); 1.10–2.30 (m, 23H); 2.46 (d, 1H, 0H); 2.53 (m, 2H); 2.80 (s, 1H, 0H ); 3.13 (td, 1H); 3.24 (t, 1H); 3.59 (m, 1H); 3.68 (s, 3H); 3.75 (m, 1H); 3.96 (bs, 1H); 4.85 (d, 1H).

EXAMPLE 11

Preparation of 17-hydroxy-17ethynyl-3beta-ethoxymethoxy-14-hydroxy-5beta,14beta-androstane A solution of n-butyl lithium 1.6M in hexane (7.19 ml; 11.5 mmoles) was added dropwise to a solution of diisopropylamine (1.61 ml; 11.5 mmoles) in anhydrous tetrahydrofuran (30 ml), kept at 0° C. under a nitrogen atmosphere. After 1 hour trimethylsilylacetylene (1.63 ml; 11.5 mmolmes) was added dropwise.

After 15 minutes, always at 0° C., a solution of 3beta-ethoxymethoxy-14-hydroxy-5beta,14beta-androstan-17-one (0.8 g; 2.2 mmoles), prepared as described in Example 4, in anhydrous tetrahydrofuran (5 ml) was added.

The temperature was then allowed to rise spontaneously.

After 16 hours a water solution saturated with ammonium chloride (10 ml) was added.

After dilution with water (10 ml) the organic phase was extracted with ethyl acetate, washed with water and dried over sodium sulfate.

The crude product obtained by evaporation of the solvent under reduced pressure was taken up with methanol (30 ml) and treated with a solution of sodium hydroxide 1N.

After 20 minutes at room temperature the product was separated by filtration as a crystalline solid (0.3 g).

An analytical sample is recrystallized from hexane:ethyl acetate=5:1.

m.p. 172°-174° C. $^1$H-NMR (200 MHz, CDCl$_3$): delta (ppm): 0.94 (s, 3H); 1.08 (s, 3H); 1.19 (t, 3H); 1.00–2.40 (m); 2.45 (s, 1H); 2.89 (s, 1H); 3.35 (s, 1H); 3.60 (q, 2H); 3.90 (bs, 1H); 4.70 (s, 2H).

EXAMPLE 12

Preparation of 17-hydroxy-17-carboxyethinyl-3beta-ethoxymethoxy-14-hydroxy-5beta,14beta-androstane A solution of 17-hydroxy-17ethynyl-3beta-ethoxymethoxy-14-hydroxy-5beta,14beta-androstane (100 mg; 0.26 mmoles), prepared as described in Example 11, in anhydrous tetrahydrofuran (10 ml), kept at 0° C. under a nitrogen atmosphere, was treated with a solution of n-butyl lithium 1.6M in hexane (0.53 ml; 0.858 mmoles).

After 15 minutes, anhydrous carbon dioxide was bubbled through and after half an hour the temperature was left to rise spontaneously to 20° C.

The solution was acidified with HCl 1N and extracted with ethyl acetate.

The organic phase was dried over sodium sulfate and the solvent was evaporated under reduced pressure.

The crude residue was chromatographed on silica gel (eluent, methylene chloride:methanol=9:1) thus obtaining a pure product (30 mg).

I.R. (film): 3500°-2500, 1710 cm$^{-1}$.

EXAMPLE 13

Preparation of 17-hydroxy-17-(2-carboxyethyl)-3beta-ethoxymethoxy-14-hydroxy-5beta,14beta-androstane A solution of 17-hydroxy-17-carboxyethynyl-3beta-ethoxymethoxy-14-hydroxy-5beta,14beta-androstane (30 mg), prepared as described in Example 12, in ethanol (5 ml), was hydrogenated at 2.72 atmosphere in a Parr apparatus in the presence of 10% palladium over charcoal.

After 1 hour at 20° C. the suspension was filtered and the solvent evaporated thus obtaining a practically quantitative yield of the product.

$^1$H-NMR (300 MHz, CDCl$_3$): delta (ppm): 0.96 (s, 3H); 1.30 (s, 3H); 1.21 (t, 3H); 1.00–2.20 (m); 2.58 (m, 4H); 3.61 (q, 2H); 3.92 (bs, 1H); 4.71 (s, 2H).

EXAMPLE 14

Preparation of 17-spiro-(5'-tetrahydrofuran-2'-one)-3-beta-ethoxymethoxy-14-hydroxy-5beta,14beta-androstane This product was prepared in an analogous manner to what has been described in Example 9, starting from 17-hydroxy-17-(2-carboxyethyl)-3beta-ethoxymethoxy)-14-hydroxy-5beta,14beta-androstane, prepared as described in Example 13.

$^1$H-NMR (300 MHz, CDCl$_3$): delta (ppm): 0.97 (s, 6H); 1.23 (t, 3H); 0.80–2.30 (m); 2.55 (m, 2H); 2.80 (s, 1H; 3.61 (q, 2H); 3.92 (bs, 1H); 4.71 (s, 2H).

Deprotection according to the procedure described in Example 10 gave 17-spiro-(5'-tetrahydrofuran-2'-one)-3beta,14-dihydroxy-5beta,14beta-androstane, having the same chemical-physical properties reported in Example 10.

EXAMPLE 15

Preparation of 3beta,14-di-(ethoxymethoxy)-16-(4-methylphenylsulfinyl)-5beta,14beta-androstane-17-one A solution of 3beta-14-di-(ethoxymethoxy)-5beta,14beta-androstan-17-one (4 g; 9.46 mmoles), prepared as described in Example 3, in anhydrous dimethoxyethane (15 ml), was slowly added under a nitrogen atmosphere to a refluxed suspension of sodium iodide (760 mg; 18.93 mmoles) in anhydrous dimethoxyethane (16 ml) containing methyl p-toluene sulfinate (2.4 g; 14.20 mmoles).

The reaction mixture was refluxed for 2 hours, then cooled to room temperature and poured in water (50 ml).

The mixture was then acidified with hydrochloric acid 2N up to pH 4–5 and extracted with methylene chloride (3×100 ml).

The combined organic phases were dried over sodium sulfate and evaporated.

The thus obtained crude residue, after chromatography on silica gel (eluent, hexane:ethyl acetate=7:3), yields a pure product (4.7 g).

$^1$H-NMR (300 MHz, CDCl$_3$): delta (ppm): 0.92 (s, 3H); 1.01 (s, 3H); 1.09 (t, 3H); 1.23 (t, 3H); 0.85–2.00 (m, 17H); 2.42 (s, 3H); 2.52 (dd, 1H); 2.61 (dd, 1H); 3.46 (m, 2H); 3.62 (q, 2H); 3.97 (bs, 1H); 4.07 (dd, 1H); 4.55 (d, 1H); 4.73 (s, 2H); 4.90 (d, 1H); 7.33 (d, 2H); 7.50 (d, 2H). I.R. (film): 2938, 1738, 1045, 1026 cm$^{-1}$.

By working in a similar way the crude 3beta-[[6-deoxy-2,4-di-(ethoxymethyl)-3-O-methyl-alpha-L-glucopyranosyl]oxy]-14-ethoxymethoxy-16-(4-methylsulfinyl)-5beta,14beta-androstan-17-one was prepared, which was used in the subsequent step without undergoing any further purification.

EXAMPLE 16

Preparation of 3beta,14-di-(ethoxymethoxy)-5beta-androst-15-en-17-one

A solution of 3beta,14-di-(ethoxymethoxy)-16-(4-methylphenylsulfinyl)-5beta,14beta-androstan-17-one (4.7 g; 8.38 mmoles), prepared as described in Example 15, and trimethylsulfite (2.6 g; 20.95 mmoles) in toluene (84 ml) was refluxed for 24 hours.

After evaporation of the solvent under reduced pressure, the crude residue was chromatographed on silica gel (eluent, hexane:ethyl acetate=7:3) thus obtaining the pure product (3.1 g).

$^1$H-NMR (300 MHz, CDCl$_3$): delta (ppm): 0.92 (s, 3H); 0.99 (s, 3H); 1.18 (t, 3H); 1.20 (t, 3H); 1.1–2.1 (m, 17H); 3.46 (m, 1H); 3.60 (q, 2H); 3.80 (m, 1H); 3.89 (bs, 1H); 4.42 (d, 1H); 4.54 (d, 1H); 4.70 (s, 2H); 6.39 (d, 1H); 7.68 (d, 1H). I.R. (film): 2934, 1716, 1042, 1021 cm$^{-1}$.

By working in a similar way 3beta-[[6-deoxy-2,4-di-(ethoxymethyl)-3-O-methyl-alpha-L-glucopyranosyl]oxy]-14-ethoxymethoxy-5beta,14beta-androst-15-ene-17-one was prepared.

m.p. 109°–110° C. $^1$H-NMR (300 MHz, CDCl$_3$): delta (ppm): 0.92 (s, 3H); 0.98 (s, 3H); 1.21 (m, 12H); 1.20–2.10 (m, 17H); 3.12 (m, 1H); 3.56 (s, 3H); 3.40–3.82 (m, 9H); 3.86 (bs, 1H); 4.41 (d, 1H); 4.53 d, 1H); 4.75 (s, 2H); 4.77 (d, 1H); 4.85 (d, 1H); 4.92 (d, 1H); 6.47 (d, 1H); 7.67 (d, 1H).

EXAMPLE 17

Preparation of 17-[(1-phenylthio)cycloprop-1-yl]-17-hydroxy-3beta,14-di-(ethoxymethoxy)-5beta,14beta-androst-15-ene A 1.26M solution of n-butyl lithium in hexane (387 ul; 0.488 mmoles) was added, at 0° C. and under a nitrogen atmosphere, to a solution of cyclopropylphenylsulfide (73 mg; 0.488 mmoles) in tetrahydrofuran (900 ul).

The reaction mixture was kept under stirring at 0° C. for 90 min., then a solution of 3beta,14-di-(ethoxymethoxy)-5beta,14beta-androst-15-en-17-one (158 mg; 0.376 mmoles), prepared as described in Example 16, in tetrahydrofuran (1 ml) was added.

After 30 more minutes at 0° C., water and diethyl ether were added and the two phases were separated.

The aqueous phase was extracted with diethyl ether and the combined organic phases were washed with a saturated solution of sodium chloride and dried over sodium sulfate.

By evaporation of the solvent, the crude residue was obtained which, chromatographed on silica gel (eluent, hexane:ethyl acetate=9:1) yields the pure product (154 mg).

$^1$H-NMR (300 MHz, CDCl$_3$): delta (ppm): 0.58 (m, 1H); 0.90 (s, 3H); 1.16 (t, 3H); 1.18 (t, 3H); 1.23 (s, 3H); 1.00–2.00 (m, 20H); 3.57 (m, 4H); 3.86 (bs, 1H); 4.67 (s, 2H); 4.69 (d, 1H); 4.79 (d, 1H); 5.69 (d, 1H); 6.15 (d, 1H); 7.14 (t, 1H); 7.24 (t, 2H); 7.46 (d, 2H). I.R. (film): 2933, 1042, 1011 cm$^{-1}$.

EXAMPLE 18

Preparation of 17-[(1-phenylthio)cycloprop-1-yl]-17-hydroxy-3beta,14-di-(ethoxymethoxy)-5beta,14beta-androstane One sixth of a solution of (eta$^4$-1,5-cyclooctadiene)(pyridine)(tricyclohesilfosfine)iridium(I)hexafluorophosphate (116 mg; 0.14 mmoles) in methylene chloride (1.2 ml) was added, under a nitrogen atmosphere, to a solution of 17-[(1-phenylthio)cycloprop-1-yl]-17-hydroxy-3beta,14-di-(ethoxymethoxy)-5-beta,14beta-androst-15-ene (274 mg; 0.48 mmoles), prepared as described in Example 17, in methylene chloride (3.5 ml).

The solution was hydrogenated by adding the remaining catalyst solution in aliquots of 200 ul at intervals of 1 hour.

After 6 hours the solvent was evaporated and the crude residue was chromatographed on silica gel (eluent, hexane:ethyl acetate=9:1) thus obtaining a pure product (71 mg).

$^1$H-NMR (300 MHz, CDCl$_3$): delta (ppm); 0.60 (m, 1H); 0.97 (s, 3H); 1.21 (t, 6H); 1.28 (s, 3H); 1.00–2.00 (m, 24H); 3.61 (m, 4H); 3.92 (bs, 1H); 4.70 (s, 2H); 4.71 (d, 1H); 4.84 (d, 1H); 7.14 (t, 1H); 7.27 (t, 2H); 7.48 (d, 2H).

EXAMPLE 19

Preparation of 17-spiro(1'-cyclobutan-2'-one)-3beta-ethoxymethoxy-14-hydroxy-5beta,14beta-androstane A 1M stannous tetrachloride solution in methylene chloride (35 ul; 0.035 mmoles) was added, at 0° C. and under a nitrogen atmosphere, to a solution of 17-[(1-phenylthio)cycloprop-1-yl]-17-hydroxy-3beta,14-di-(ethoxymethoxy)-5beta,14beta-androstane (20 mg; 0.035 mmoles), prepared as described in Example 18, in methylene chloride (350 ul).

After one minute a saturated solution of sodium bicarbonate was added and the mixture was extracted with diethylether.

The combined organic phases were dried over sodium sulfate.

After evaporation of the solvent, the crude residue thus obtained was chromatographed on silica gel (eluent, hexane:ethyl acetate=95:5) yielding a pure product (1.2 mg).

$^1$H-NMR (300 MHz, CDCl$_3$): delta (ppm): 0.81 (s, 3H); 1.06 (s, 3H); 1.20 (t, 3H); 0.90–2.40 (m, 23H); 2.78

(m, 2H); 3.60 q, 2H); 3.94 (bs, 1H); 4.70 (s, 2H). I.R. (film): 2933, 1771, 1040 cm$^{-1}$.

Deprotection according to the procedure described in Example 10 gave 17-spiro(1'-cyclobutan-2'-one)-3-beta,14-di-hydroxy-5-beta,14beta-androstane.

EXAMPLE 20

Preparation of 17-(1-ethoxycycloprop-1-yl)-17-hydroxy-3-beta,14-di(ethoxymethoxy)-5beta,14beta-androst-15-ene A 1.6M solution of t-butyl lithium in pentane (4.6 ml; 7.37 mmoles) and then a solution of 1-bromo-1-ethoxycyclopropane (647 mg; 3.91 mmoles) in diethyl ether (0.4 ml) were added to diethyl ether (8 ml) at −78° C. under nitrogen atmosphere.

After 5 minutes a solution of 3beta,14-di-(ethoxymethoxy)-5beta,14beta-androst-15-en-17-one (1.03 g; 2.44 mmoles), prepared as described in Example 16, and lithium bromide (1.06 g; 12.24 mmoles) in tetrahydrofuran (8 ml) were added at −78° C.

After 10 more minutes at this temperature, the reaction mixture was brought to 0° C. in an ice bath and a saturated solution of ammonium chloride and diethyl ether were added.

The combined organic phases were dried over sodium sulfate.

After evaporation of the solvent, the crude residue thus obtained was chromatographed on silica gel (eluent, hexane:ethyl acetate=8:2) yielding a pure product (931 mg).

$^1$H-NMR (300 MHz, CDCl$_3$): delta (ppm): 0.61 (m, 1H); 0.72 (m, 1H); 0.93 (s, 3H); 1.12 (t, 3H); 1.18 (s, 3H); 1.18 (t, 3H); 1.20 (t, 3H); 0.80–2.00 (m, 19H); 3.30–3.50 (m, 2H); 3,60 (m, 4H); 3.88 (bs, 1H); 4.71 (s, 2H); 4.74 (s, 2H); 5.60 (d, 1H); 6.11 (d, 1H). I.R. (film): 3482, 2933, 1448, 1042 cm$^{-1}$.

By working in a similar way 17(S)-3beta-[[6-deoxy-2,4-di-(ethoxymethoxy)-3-O-methyl-alpha-L-glucopyranosyl]oxy]-14-ethoxymethoxy-17-(1-ethoxycycloprop-1-yl)-17-hydroxy-5beta,14beta-androst-15-ene was prepared.

$^1$H-NMR (300 MHz, CDCl$_3$): delta (ppm): 0.93 (s, 3H); 1.12 (t, 3H); 0.50–2.00 (m, 36H); 3.12 (m, 1H); 3.57 (s, 3H); 3.30–3.80 (m, 11H); 3.86 (bs, 1H); 4.73 (s, 2H); 4.75 (s, 2H); 4.78 (d, 1H); 4.85 (d, 1H); 4.93 (d, 1H); 5.59 (d, 1H); 6.10 (d, 1H).

EXAMPLE 21

Preparation of 17-spiro-(1'-cyclobutan-2'-one)-3beta,14-di-(ethoxymethoxy)-5beta,14beta-androst-15-ene Silica gel (40 mg) and water (8.5 ul; 0.079 mmoles) were added to a solution of 17-(1-ethoxycycloprop-1-yl)-17-hydroxy-3beta,14-di-(ethoxymethoxy)-5beta,14beta-androst-15ene (26 mg; 0.052 mmoles), prepared as described in Example 20, in toluene (800 ul).

The mixture was heated to 80° C. for 13 hours.

After filtration of the silica gel and evaporation of the solvent, the crude residue obtained was chromatographed on silica gel (eluent, hexane:ethyl acetate=95:3) yielding the pure product (3.3 mg).

$^1$H-NMR (300 MHz, CDCl$_3$): delta (ppm): 0.90 (s, 3H); 1.14 9s, 3H); 1.20 (t, 3H); 1.21 (t, 3H); 0.90–2.50 (m, 19H); 2.82 (m, 2H); 3.40 (m, 1H); 3.61 (m, 3H); 3.96 (bs, 1H); 4.71 (s, 4H); 5.81 (d, 1H); 6.38 (d, 1H). I.R. (film): 2926, 1774, 1042 cm$^{-1}$.

Deprotection according to the procedure described in Example 10 gave 17-spiro-(1'-cyclobutan-2'-one)-3beta,14-di-hydroxy-5beta,14-androst-15-ene.

EXAMPLE 22

Preparation of 17-(1-ethoxycycloprop-1yl)-17-hydroxy-3beta,14-di-(ethoxymethoxy)-5beta,14beta-androstane A mixture of 17-(1-ethoxycycloprop-1-yl)-17-hydroxy-3-beta,14-di-(ethoxymethoxy)-5-beta,14beta-androst-15-ene (967 mg; 1.908 mmoles), prepared as described in Example 20, sodium carbonate (48 mg) and palladium hydroxide over charcoal at 20% (97 mg) in ethanol (19 ml) was hydrogenated at room temperature for 2 hours.

After filtration of the catalyst and evaporation of the solvent under reduced pressure the crude residue thus obtained was chromatographed on silica gel (eluent, hexane:ethyl acetate=8:2) yielding the pure product (871 mg).

$^1$H-NMR (300 MHz, CDCl$_3$): delta (ppm): 0.66 (m, 2H); 0.96 (s, 3H); 1.12 (t, 3H); 1.19 (t, 3H); 1.19 (s, 3H); 1.21 (t, 3H); 0.90–2.20 (m, 23H); 3.30 (m, 1H); 3.40–3.70 (m, 5H); 3.92 (bs, 1H); 4.66 (d, 1H); 4.71 (s, 2H); 4.84 (d, 1H). I.R. (film): 2973, 1042 cm$^{-1}$.

By working in a similar way 17(S)-3beta-[[6-deoxy-2,4-di-(ethoxymethyl)-3-O-methyl-alpha-L-glucopyranosyl]oxy]-14-ethoxymethoxy-17-(1-ethoxycycloprop-1-yl)-17-hydroxy-5beta,14beta-androstane was prepared.

$^1$H-NMR (300 MHz, CDCl$_3$): delta (ppm): 0.97 (s, 3H); 1.12 (t, 3H); 0.60–2.00 (m, 40H); 3.12 (m, 1H); 3.30 (m, 2H); 3.57 (s, 3H); 3.45–3.80 (m, 9H); 3.88 (bs, 1H); 4.66 (d, 1H); 4.75 (s, 2H); 4.79 (d, 1H); 4.83 (d, 1H); 4.86 (d, 1H); 4.93 (d, 1H).

EXAMPLE 23

Preparation of 17-spiro-(1'-cyclobutan-2'-one)-3beta-ethoxymethoxy-14-hydroxy-5-beta,14beta-androstane A solution of 17-(1-ethoxycycloprop-1-yl)-17-hydroxy-3-beta,14-di-(ethoxymethoxy)-5beta,14beta-androstane (29 mg; 0.056 mmoles), prepared as described in Example 22, and monohydrous p-toluenesulfonic acid (11 mg, 0.056 mmoles) in toluene saturated with water (0.57 ml) was heated to 50° C. for 30 minutes.

Afterwards a saturated solution of sodium bicarbonate was added and the mixture was extracted with ethyl acetate.

The combined organic phases were dried over sodium sulfate.

After evaporation of the solvent, the crude residue thus obtained was chromatographed on silica gel (eluent, hexane:ethyl acetate=7:3) yielding the pure product (8 mg).

$^1$H-NMR (300 MHz, CDCl$_3$): delta (ppm): 0.94 (s, 3H); 1.09 (s, 3H); 1.21 (t, 3H); 1.00–2.00 (m, 20H); 2.12 (m, 1H); 2.37 (m, 1H); 2.60 (m, 1H); 2.82 (m, 2H); 3.61 (q, 2H); 3.92 (bs, 1H); 4.71 (s, 2H). I.R. (film): 3475, 2936, 1764, 1448, 1044 cm$^{-1}$.

Unprotection according to the procedure described in Example 10 gave 17-spiro-(1'-cyclobutan-2'-one)-3-beta,14-di-hydroxy-5beta,14-androstane.

By working in a similar way 3beta-[[6-deoxy-2,4-di-(ethoxymethyl)-3-O-methyl-alpha-L-glucopyranosyl- ]oxy]-14-ethoxymethoxy-17-(R)-spiro-(1'-cyclobutan-2'-one)-5beta,14beta-androstane was prepared.

$^1$H-NMR (300 MHz, CDCl$_3$): delta (ppm): 0.95 (s, 3H); 1.13 (s, 3H); 1.18 (d, 3H); 1.22 (bt, 9H); 0.90–2.10 (m, 21H); 2.39 (m, 1H); 2.58 (m, 1H); 2.81 (t, 2H); 3.13 (bt, 1H); 3.58 (s, 3H); 3.45–3.83 (m, 9H); 3.86 (bs, 1H); 4.70 (d, 1H); 4.75 (s, 1H); 4.76 (d, 1H); 4.78 (d, 1H); 4.85 (d, 1H); 4.92 (d, 1H).

EXAMPLE 24

Preparation of 17-spiro-(5'-tetrahydrofuran-2'-one)-3-beta-ethoxymethoxy-14-hydroxy-5beta,14beta-androstane A solution of 30% hydrogen peroxide (3.4 ul; 0.1094 mmoles) followed by a 9M solution of sodium hydroxide (6.3 ul; 0.0569 mmoles) was added, at room temperature, to a solution of 17-spiro-(1'-cyclobutan-2'-one)-3beta-ethoxymethoxy-14-hydroxy-5beta,14beta-androstane (18 mg; 0.0437 mmoles), prepared as described in Example 23, in a mixture of methanol and tetrahydrofuran 1:1 (450 ul).

The reaction mixture was stirred continuously at room temperature for one hour and then a saturated solution of ammonium chloride and ethyl acetate was added.

The aqueous phase was extracted with ethyl acetate.

The combined organic phases were washed with a saturated solution of sodium chloride and dried over sodium sulfate.

After evaporation of the solvent, the crude residue thus obtained was chromatographed on silica gel (eluent, hexane:ethyl acetate=1:1) yielding the pure product (6.5 mg).

$^1$H-NMR (300 MHz, CDCl$_3$): delta (ppm): 0.95 (s, 3H); 0.98 (s, 3H); 1.21 (t, 3H); 1.10–1.90 (m, 19H); 2.00–2.30 (m, 4H); 2.55 (m, 2H); 3.61 (q, 2H); 3.93 (bs, 1H); 4.71 (s, 2H). I.R. (film): 3490, 2937, 1764, 1042 cm$^{-1}$.

By working in a similar way 3beta-[[6-deoxy-2,4-di-(ethoxymethyl)-3-O-methyl-alpha-L-glucopyranosyl-]oxy]-14-ethoxymethoxy-17-(R)-spiro-(5'-tetrahydrofuran-2'-one)-5beta,14beta-androstane was prepared.

$^1$H-NMR (300 MHz, CDCl$_3$): delta (ppm): 0.97 (s, 3H); 1.04 (s, 3H); 1.23 (m, 12H); 0.70–2.30 (m, 22H); 2.55 (m, 3H); 3.13 (bt, 1H); 3.57 (s, 3H); 3.45–3.82 (m, 9H); 3.88 (bs, 1H); 4.72 (d, 1H); 4.75 (s, 1H); 4.77 (d, 1H); 4.82 (d, 1H); 4.86 (d, 1H); 4.93 (d, 1H).

EXAMPLE 25

Preparation of 3beta-[(6-deoxy-3-O-methyl-alpha-L-glucopyranosyl-)oxy]-14-hydroxy-17-(R)-spiro-(5'-tetrahydrofuran-2'-one)-5beta,14beta-androstane This compound was prepared by working in a way similar to Example 10 but using, as starting compound, 3beta-[[6-deoxy-2,4-di-(ethoxymethyl)-3-O-methyl-alpha-L-glucopyranosyl]oxy]-14-ethoxymethoxy-17-(R)-spiro-(5'-tetrahydrofuran-2'-one)-5-beta,14beta-androstane prepared according to Example 24; yield 93%.

m.p. 245°–247° C. $^1$H-NMR (300 MHz, CDCl$_3$): delta (ppm): 0.97 (s, 3H); 0.98) s, 3H); 1.25 (d, 3H); 1.10–2.30 (m, 22H); 2.56 (m, 3H); 3.15 (m, 1H); 3.25 (t, 1H); 3.58 (m, 1H); 3.69 (s, 3H); 3.75 (m, 1H); 3.98 (bs, 1H); 4.85 (d, 1H).

By working in a similar way 3beta-[[6-deoxy-3-O-methyl-alpha-L-glucopyranosyl]oxy]-14-hydroxy-17-(R)-spiro-(1'-cyclobutan-2'-one)-5-beta,14beta-androstane was prepared.

EXAMPLE 26

Examination of the interaction of compounds of this invention with the isoforms alpha1 and alpha3 (of Na+/K+-ATPase from rat Compound A—17-spiro-(5'-tetrahydrofuran-2'-one)-3beta,14-di-hydroxy-5beta,14beta-androstane (Example 10)

Compound B—3beta-[[6-deoxy-3-O-methyl-alpha-L-glucopyranosyl]oxy]-14-hydroxy-17-(S)-spiro-(5'-tertahydrofuran-2'-one)-5beta,14beta-androstane (Example 10)

Displacement of [$^3$H]ouabain by Compound A and B was tested in kidney and brain preparation from rat according to Noel F. et al., Biochemical Pharmacology, 40(12), 2611–2616, (1990).

| | [$^3$H]ouabain displacement percent | |
|---|---|---|
| | kidney preparation $3 \times 10^{-6}$ M (n = 3) | brain preparation $10^{-6}$ M (n = 3) |
| Compound A | 22.2 ± 5 | 3.7 ± 4 |
| Compound B | 38.0 ± 5.2 | 15.0 ± 4.6 |
| Ouabain | 26.6 ± 3.9 | 96.5 ± 0.2 |

We claim:

1. A compound of formula

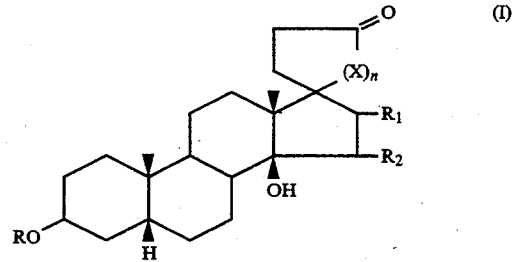

in which

X is an oxygen atom;

n is 0 or 1;

R is a hydrogen atom or a glycosyl residue from mono-, di- or tri- saccharides selected from the group consisting of D-glucose, D-lyxose, D-xylose, 2-deoxy-D-glucose, D-allomethylose, D-thevetose, L-thevetose, L-talomethylose, D-gulomethylose, D-glucomethylose, L-rhamnose, L-acofriose, D-fucose, L-fucose, D-digitalose, L-acovenose, D-digitoxose, D-cymarose, D-boivinose, D-sarmentose, L-oleandrose, D-oleandrose, D-diginose;

$R_1$ and $R_2$ are hydrogen atoms or together they form a covalent bond;

substituents in position 5, 10, 13 and 14 have beta configuration.

2. A compound according to claim 1 of formula

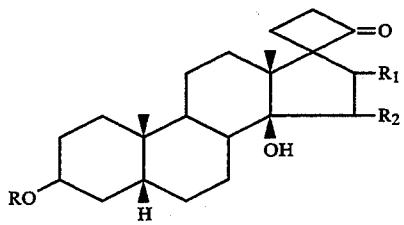 (I-A)

in which R, $R_1$ and $R_2$ have the meanings mentioned in claim 1.

3. A compound according to claim 1 of formula

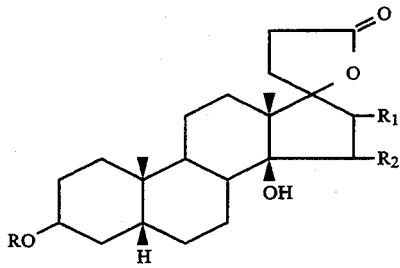 (I-B)

in which R, $R_1$ and $R_2$ have the meanings mentioned in claim 1.

4. A pharmaceutical composition containing a therapeutically effective amount of a compound of formula I as shown in claim 1 together with a pharmaceutically acceptable carrier.

5. A compound of formula

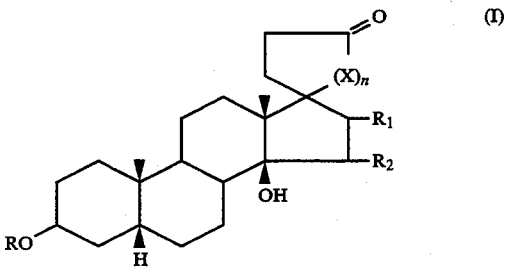 (I)

in which
X is an oxygen atom;
n is 0 or 1;
R is H or glucopyranosyl;
$R_1$ and $R_2$ are H or, together, form a covalent bond;
substituents in positions 5, 10, 13 and 14 have beta configuration.

6. A pharmaceutical composition comprising a therapeutically effective amount of a compound of claim 5 together with a pharmaceutically acceptable carrier.

* * * * *